US00PP18714P2

(12) United States Plant Patent
Bradford

(10) Patent No.: US PP18,714 P2
(45) Date of Patent: Apr. 8, 2008

(54) NECTARINE TREE NAMED 'MAJESTIC SWEET'

(50) Latin Name: *Prunus persica*
Varietal Denomination: Majestic Sweet

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,885

(22) Filed: Dec. 13, 2006

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP13,474 P2 1/2003 Bradford

*Primary Examiner*—Kent Bell

(57) ABSTRACT

The present invention relates to a new and distinct variety of nectarine tree, *Prunus persica,* broadly characterized by a medium size, vigorous, hardy, self-fertile, productive and regular bearing tree. The fruit matures under the ecological conditions described in mid to late August, with first picking on Aug. 19, 2006. The fruit is uniformly large in size, sub-acidic and sweet in flavor, globose in shape, clingstone in type, firm in texture, yellow in flesh color, and red to orange in skin color.

1 Drawing Sheet

Botanical classification: *Prunus persica.*
Variety denomination: 'MAJESTIC SWEET'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'MAJESTIC SWEET'.

During the spring of 1996 I gathered fruit from several different unnamed seedlings in my experimental orchard located near Le Grand, Calif., in Merced County (San Joaquin Valley). One particular group of nectarines was late in maturing, yellow in flesh color, and clingstone in type, and was thus designated as "YNC (OP)". I removed the seeds from this fruit, stratified, germinated, and grew them as seedlings on their own root in my greenhouse, and upon reaching dormancy that fall I transplanted them to a cultivated area in the experimental orchard described above. During the fruit evaluation season of 2000 I selected the claimed variety as a single tree from this group of "YNC (OP)" described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is most similar to 'Sweet August' (U.S. Plant Pat. No. 13,474) nectarine by producing nectarines that are firm in texture, clingstone in type, yellow in flesh color, mostly red in skin color, and sub-acid in flavor, but is distinguished therefrom by being eglandular rather than having globose leaf glands and by producing fruit that is somewhat larger in size, that matures about seven days later, and that is not as susceptible to corking in the flesh.

SUMMARY OF VARIETY

In summary, the present variety is characterized by a medium size, vigorous, hardy, self-fertile, productive and regular bearing tree. The fruit matures under the ecological conditions described in mid to late August, with first picking on Aug. 19, 2006. The fruit is uniformly large in size, sub-acidic and sweet in flavor, globose in shape, clingstone in type, firm in texture, yellow in flesh color, and red to orange in skin color.

DRAWING

The accompanying photograph consists of four whole fruits positioned to display the characteristics of the skin color and form, one fruit divided transversely to the suture plane to reveal the flesh and stone, various leaves, and insets showing buds and blossoms.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of shipping ripe on Aug. 22, 2006, on a multiplied tree utilizing 'Nemaguard' (unpatented) rootstock during its sixth growing season. All major color code designations are by reference to the Inter-Society Color Council, National Bureau of Standards. Common color names are also used occasionally.

Tree

Size: Medium, reaching and maintaining a height of 9' [2.74 m.] and a spread of 6' [1.83 m.] after six growing seasons utilizing typical dormant pruning.

Vigor: Medium, responding typically to irrigation and fertilization. The variety grows about 2' [0.61 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat Tolerance: Observed to perform adequately in typical central California climatic conditions, which typically include extended periods of heat.

Drought Tolerance: Variety is developed for commercial orchards and requires regular irrigation.

Production: Productive, thinning necessary.

Fertility: Self-fertile.

Bearing: Regular bearer with no alternate bearing yet observed.

Approximate Chilling Requirement: 625 hours.

Trunk:

*Size.*—Medium, reaching a maximum diameter of 3⅛" [79 mm.] after the sixth growing season.

*Texture.*—Shaggy.

*Bark color.*—A Brownish gray [64. brGy] and Modertae reddish brown [43. m.rBr] variegation.

*Lenticels.*—Approximate Number Per Square Inch: 8. Color: Moderate yellowish brown [77. m.yBr]. Typical Size: ⅛" [3.2 mm.] to 7/16" [11.1 mm.]. Shape: Eye-shaped to elongated.

Branches:

*Size.*—Diameter of limb is 2" [51 mm.] measured 12" above the crotch, 1⅛" [28 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Number Per Square Inch: More than 50 on second year wood. Color: Strong orange yellow [68. s.OY]. Typical size: 1/64" [0.4 mm.] to 3/32" [2.4 mm.] on second year wood. Shape: Elongated.

Leaves:

*Size.*—Medium. Average Length: 5½" [140 mm.]. Average Width: 1 11/16" [43 mm.].

*Arrangement.*—Alternate.

*Thickness.*—Medium.

*Form.*—Elliptical.

*Apex.*—Acuminate.

*Base.*—Acute, with a base angle of 75 to 85 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: 5/16" [7.9 mm.]. Average Thickness: 1/16" [1.6 mm.]. Color: Brilliant yellow green [116. brill.YG].

*Stipules.*—Number: 2 per leaf, up to 6 per growing tip. Average Length: 7/16" [11.1 mm.]. Color: Brilliant yellow green [116. brill.YG] becoming Moderate brown [58. m.Br] with maturity.

*Glands.*—Eglandular.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 11/16" [17.5 mm.] 1 week before bloom.

*Form.*—Not appressed.

*Surface.*—Pubescent.

*Color.*—Light purplish pink [249. l.pPk].

Flowers: Perfect, complete, perigynous, usually a single pistil, typically thirty or more stamens, five sepal and petal locations alternately positioned.

*Type.*—Showy, very large.

*Average flower diameter.*—2" [54.0 mm.].

*Number of petals.*—Usually five, a few with extra petal fragments and a few double blossoms.

*Petal shape.*—circular to oval.

*Petal margin.*—Somewhat wavy.

*Average petal diameter.*—13/16" [20.6 mm.].

*Average petal length.*—13/16" [20.6 mm.].

*Petal apex.*—Rounded.

*Petal base.*—Rounded to somewhat truncate.

*Petal color.*—Pale pink [7. p.Pk] toward the apex, Light purplish pink [249. l.pPk] toward the base.

*Anther color.*—Dark reddish orange [38. d.rO] over a Light yellow [86. l.Y] center at bloom onset.

*Stigma color.*—Pale yellow green [121. p.YG].

*Sepal color.*—Dark purplish red [259. d.pR].

*Sepal length.*—5/16" [7.9 mm.].

*Sepal width.*—¼ [6.4 mm.].

*Average pistil length.*—13/16" [20.6 mm.].

*Average stamen length.*—⅝" [15.9 mm.].

*Fragrance.*—Moderate.

*Blooming period.*—Medium, four days after 'Spring Bright' (U.S. Plant Pat. No. 7,507) nectarine.

*Onset of bloom.*—One percent on Feb. 28, 2006.

*Date of full bloom.*—Mar. 11, 2006.

*Duration of bloom.*—One to two weeks, dependent on ambient temperature.

*Number per cluster.*—1 to 3 with single flowers most common.

FRUIT

Maturity When Described: Shipping ripe, Aug. 22, 2006.

Date of First Picking: Aug. 19, 2006.

Date of Last Picking: Sep. 1, 2006.

Size: Uniform, large.

*Average diameter axially.*—2⅞" [73 mm.].

*Average diameter across suture plane.*—3" [76 mm.].

*Average diameter across cheek plane.*—3" [76 mm.].

*Typical weight.*—7.9 ounces [224 grams].

Form: Uniform, globose, mostly symmetrical.

*Longitudinal section form.*—Elliptical.

*Axial view.*—Round.

Suture: A sharp groove inside the stem cavity, a shallow trough along the side, and a shallow groove toward the apex, ending just beyond the pistil point with a slight depression.

Ventral Surface: Rounded, lipped stronger toward the apex.

Lips: Mostly equal.

Cavity: Flaring, circular to somewhat elongated in the suture plane, suture showing on one side, Light yellow [86. l.Y] stem markings present.
*Depth.*—¾" [19.1 mm.].
*Breadth.*—1⅛" [28.6 mm.].
Base: Truncate, but slightly cordate if viewed parallel to the suture.
Apex: Rounded.
Pistil Point: Both apical and oblique, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed in dry season.
*Color.*—Deep red [13. deep R] smoothly blending into a Moderate reddish orange [37. m.rO] background with some Light orange yellow [70. l.OY] freckling on the sides and toward the apex.
Flesh:
*Color.*—Brilliant yellow [83. brill.Y] from the skin to very near the stone with very slight Moderate red [15. m.R] streaking near the stone.
*Surface of pit cavity.*—Deep pink [3. deep Pk] broken fibers when twisted from stone.
*Amygdalin.*—Scarce.
*Juice.*—Abundant, rich.
*Texture.*—Firm, crisp.
*Fibers.*—Abundant, fine.
*Ripens.*—Slightly earlier at the apex.
*Flavor.*—Sub-acidic and sweet, typically 17 brix.
*Aroma.*—Very slight.
*Eating quality.*—Very good.

STONE

Type: Clingstone.
Form: Oval.
Hilum: Narrow.
Base: Straight.
Apex: Obtuse with an average angle of 110 degrees.
Sides: Equal.
Surface: Regularly furrowed toward the apex, pitted toward the base.
Ridges: Jagged.
External Color: Dark reddish brown [44. d.rBr].
Pit Wall Color When Cracked: Dark Brown [59. d.Br].
Cavity Surface Color: Deep yellowish brown [75. deep yBr].
Average Pit Wall Thickness: ¼" [6.4 mm.].
Average Width: 1½" [38.1 mm.].
Average Length: 1 1/16" [27.0 mm.].
Average Breadth: ¾" [19.1 mm.].
Tendency to Split: Slight.
Kernel:
*Form.*—Oval.
*Skin color.*—Brilliant yellow [83. brill.Y] when first removed.
*Pellicle color.*—Grayish yellowish brown [80. gy.yBr].
*Vein color.*—Deep brown [56. deep Br].
*Taste.*—Bitter.
*Viable.*—Yes.
*Average width.*—½" [12.7 mm.].
*Average length.*—13/16" [20.6 mm.].
*Amygdalin.*—Abundant.

USE

Market: Fresh market and long distance shipping.
Keeping Quality: Good, fruit quality observed to remain in good condition after 21 days in standard cold room at 36° Fahrenheit [2° Celsius].
Shipping Quality: Good.
Resistance To Insects: No unusual susceptibilities noted.
Resistance To Diseases: No unusual susceptibilities noted.
Resistance to Nutritional Deficiencies: Variety appears to be tolerant to calcium deficiencies, making it somewhat resistant to corking in the flesh.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Sweet August' (U.S. Plant Pat. No. 13,474) nectarine by producing nectarines that are firm in texture, clingstone in type, yellow in flesh color, mostly red in skin color, and sub-acid in flavor, but is distinguished therefrom by being eglandular rather than having globose leaf glands and by producing fruit that is somewhat larger in size, that matures about seven days later, and that is not as susceptible to corking in the flesh.

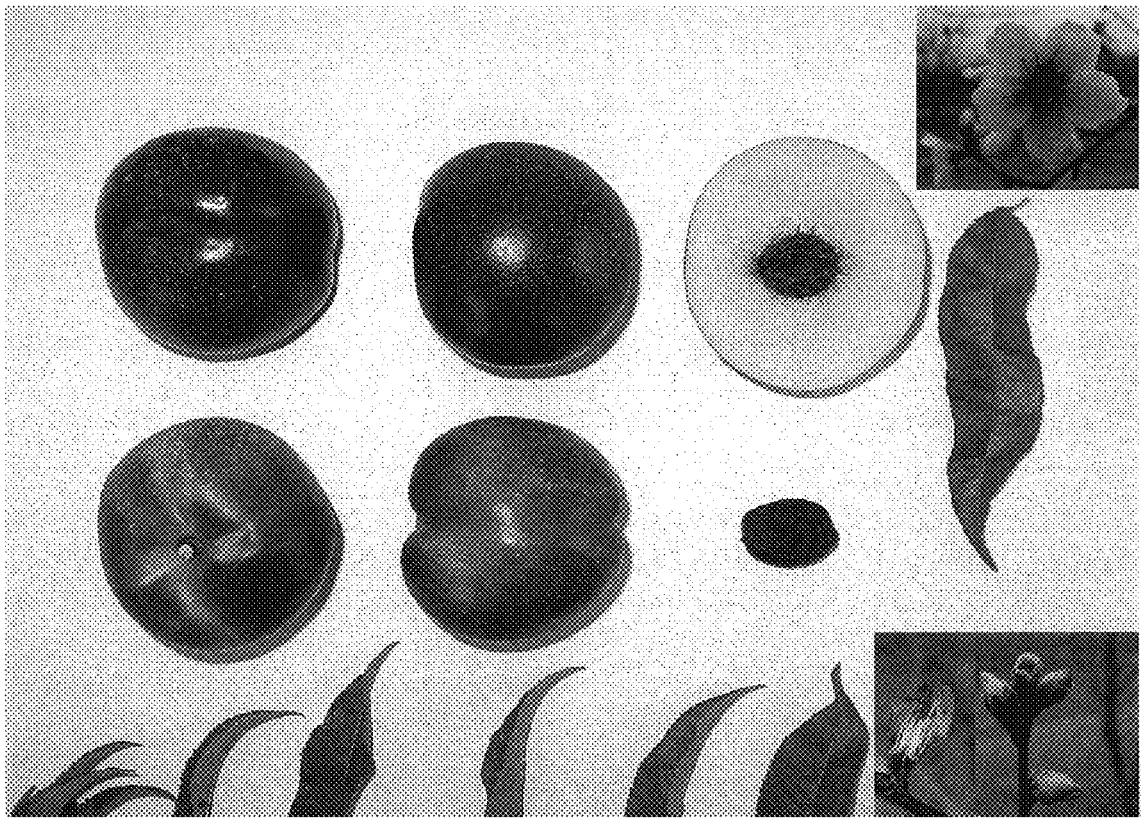

* * * * *